US012686823B2

(12) United States Patent
Kobayashi et al.

(10) Patent No.: US 12,686,823 B2
(45) Date of Patent: Jul. 21, 2026

(54) HYDROCARBON PRODUCTION APPARATUS AND HYDROCARBON PRODUCTION METHOD

(71) Applicant: ENEOS Corporation, Tokyo (JP)

(72) Inventors: Atsushi Kobayashi, Tokyo (JP); Masakazu Ikeda, Tokyo (JP); Yasushi Sato, Tokyo (JP); Akira Goto, Tokyo (JP); Takuya Kajita, Tokyo (JP); Satoshi Takasaki, Tokyo (JP); Ryo Kishida, Tokyo (JP); Kazuya Mayumi, Tokyo (JP); Satoshi Nagatake, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 138 days.

(21) Appl. No.: 18/567,077

(22) PCT Filed: Apr. 18, 2022

(86) PCT No.: PCT/JP2022/018025
§ 371 (c)(1),
(2) Date: Dec. 5, 2023

(87) PCT Pub. No.: WO2022/264676
PCT Pub. Date: Dec. 22, 2022

(65) Prior Publication Data
US 2024/0271045 A1      Aug. 15, 2024

(30) Foreign Application Priority Data
Jun. 16, 2021      (JP) ................................. 2021-100350

(51) Int. Cl.
*C10G 2/00*      (2006.01)
*C01B 3/50*      (2006.01)
*C07C 1/04*      (2006.01)

(52) U.S. Cl.
CPC ................. *C10G 2/30* (2013.01); *C01B 3/50* (2013.01); *C07C 1/0485* (2013.01); *C01B 2203/0475* (2013.01); *C01B 2203/062* (2013.01); *C01B 2203/063* (2013.01); *C01B 2203/146* (2013.01); *C01B 2210/0051* (2013.01); *C10G 2300/4081* (2013.01)

(58) Field of Classification Search
CPC .............. C10G 2/30; C10G 2300/4081; C07C 1/0485; B01J 2219/00006
See application file for complete search history.

(56) References Cited

U.S. PATENT DOCUMENTS 4,579,985 A * 4/1986 Minderhoud ......... C07C 1/0485
                                                208/950
5,324,335 A * 6/1994 Benham ................ C10L 1/1824
                                                518/703
2013/0345325 A1 12/2013 Lecomte et al.
2014/0206780 A1 7/2014 Kresnyak

FOREIGN PATENT DOCUMENTS

EP          3670443 A1     6/2020
JP        S60124693 A      7/1985
JP        H06184559 A      7/1994
JP       2008248179 A     10/2008
JP       2014-517806 A     7/2014
JP       2015517586 A      6/2015
WO      2006/099573 A1     9/2006
WO      2011/141635 A1    11/2011
WO      2019021129 A1      1/2019
WO      2020/208008 A1    10/2020

OTHER PUBLICATIONS

International Search Report (PCT/ISA/210) and Written Opinion (PCT/ISA/237) both with English translation mailed on Jun. 28, 2022, by the Japanese Patent Office as the International Searching Authority for International Application No. PCT/JP2022/018025.
Office Action (Examination report No. 1 for standard patent application) issued on Feb. 12, 2025, in corresponding Australian Patent Application No. 2022294430. (3 pages).
Office Action (Examination report No. 2 for standard patent application) issued on Jun. 30, 2025, in corresponding Australian Patent Application No. 2022294430. (3 pages).
Extended European Search Report issued on May 7, 2025, in corresponding European Patent Application No. 22824671.6. (7 pages).
Office Action (Notice of Reasons for Refusal) issued on Feb. 24, 2026, in corresponding Japanese Patent Application No. 2023-529644 and machine English translation of the Office Action. (9 pages).
Office Action (Examination report No. 3 for standard patent application) issued on Oct. 9, 2025, in corresponding Australian Patent Application No. 2022294430. (4 pages).

* cited by examiner

*Primary Examiner* — Randy Boyer
(74) *Attorney, Agent, or Firm* — BUCHANAN, INGERSOLL & ROONEY PC

(57)                 ABSTRACT
A hydrocarbon production apparatus includes a synthesis gas production unit structured to produce a synthesis gas containing carbon monoxide and hydrogen by using carbon dioxide and hydrogen, a hydrocarbon production unit structured to produce a hydrocarbon by using the synthesis gas, and a first separator structured to separate a recycle gas containing a light hydrocarbon having 4 or less carbon atoms from an effluent from the hydrocarbon production unit. The synthesis gas production unit is structured to receive supply of the recycle gas and also use the recycle gas for production of the synthesis gas.

17 Claims, 7 Drawing Sheets

HYDROCARBON PRODUCTION APPARATUS AND HYDROCARBON PRODUCTION METHOD

CROSS-REFERENCE TO RELATED APPLICATIONS

This application is based upon and claims the benefit of priority from the prior Japanese Patent Application No. 2021-100350, filed on Jun. 16, 2021, and the International Patent Application No. PCT/JP2022/018025, filed on Apr. 18, 2022, the entire content of each of which is incorporated herein by reference.

BACKGROUND

Field of the Invention

The present invention relates to a hydrocarbon production apparatus and a hydrocarbon production method.

Description of the Related Art

A liquid fuel production technique using GTL (Gas to Liquid) is known (see Patent Literature 1). This production technique includes, as an example, a step of producing hydrogen and carbon monoxide from natural gas, and a step of producing a liquid hydrocarbon having a high energy density by Fischer-Tropsch reaction (hereinafter, appropriately referred to as "FT reaction") using, as a raw material, a synthesis gas containing hydrogen and carbon monoxide.

Patent Literature 1: JP 2008-248179 A

In recent years, reduction of carbon dioxide generated in various economic activities has become one of major problems. When carbon dioxide contained in exhaust gas or the like is used for the production of hydrocarbon described above, it can greatly contribute to the realization of carbon-neutral. The present inventors have conducted intensive studies on a hydrocarbon production technique from such a viewpoint, and as a result, have arrived at a technique for improving the production efficiency of hydrocarbons.

SUMMARY OF THE INVENTION

The present invention has been made in view of such a situation, and an object thereof is to provide a technique for improving the production efficiency of hydrocarbons.

One aspect of the present invention is a hydrocarbon production apparatus. This apparatus includes a synthesis gas production unit structured to produce a synthesis gas containing carbon monoxide and hydrogen by using carbon dioxide and hydrogen, a hydrocarbon production unit structured to produce a hydrocarbon by using the synthesis gas, and a first separator structured to separate a recycle gas containing a light hydrocarbon having 4 or less carbon atoms from an effluent from the hydrocarbon production unit. The synthesis gas production unit is structured to receive supply of the recycle gas and also use the recycle gas for production of the synthesis gas.

Another aspect of the present invention is a hydrocarbon production method. This method includes a synthesis gas production step of producing a synthesis gas containing carbon monoxide and hydrogen by using carbon dioxide and hydrogen, a hydrocarbon production step of producing a hydrocarbon by using the synthesis gas, and a first separation step of separating a recycle gas containing a light hydrocarbon having 4 or less carbon atoms from an effluent from the hydrocarbon production step. In the synthesis gas production step, supply of the recycle gas is received and the recycle gas is also used for production of the synthesis gas.

Still another aspect of the present invention is a synthesis gas production apparatus. This apparatus receives supply of carbon dioxide and hydrogen and generates carbon monoxide from carbon dioxide contained in a feed gas by utilizing heat generation associated with oxidation of hydrogen contained in the feed gas.

Any combination of the aforementioned components or any manifestation of the present disclosure realized by modifications of a method, apparatus, system, and so forth, is effective as an embodiment of the present disclosure.

BRIEF DESCRIPTION OF DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

Figure 1:
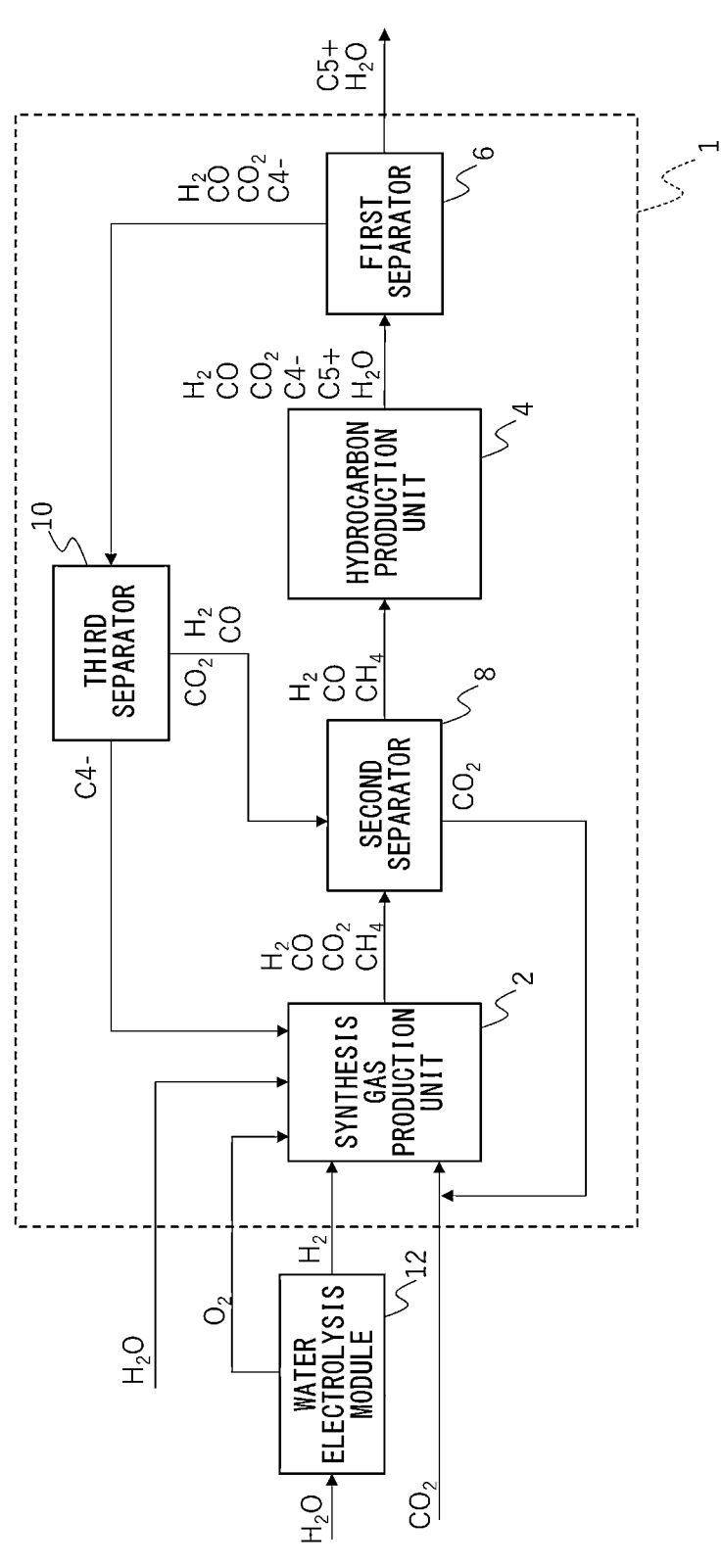
FIG. 1 is a schematic diagram of a hydrocarbon production apparatus according to Embodiment 1.

Hereinafter, the present invention will be described based on preferred embodiments with reference to the drawings. The embodiments are not intended to limit the technical scope of the present invention but are examples, and all features described in the embodiments and combinations thereof are not necessarily essential to the invention. Therefore, the contents of the embodiments can be subjected to many design changes such as changes, additions, and deletions of components without departing from the spirit of the invention defined in the claims. A new embodiment to which the design change is made has an effect of each of the combined embodiment and modifications.

In the embodiment, the contents that can be changed in design are emphasized with notations such as "of the present embodiment" and "in the present embodiment", but the design change is allowed even in the contents without such notations. Any combination of the components described in the embodiment is also effective as an aspect of the present invention. The same or equivalent components, members, and processing illustrated in the drawings are denoted by the same reference signs, and the redundant description will be omitted as appropriate. Scales and shapes of parts illustrated in the drawings are set for the sake of convenience in order to facilitate the description, and are not limitedly interpreted unless otherwise specified. When the terms "first", "second", and the like are used in the present specification or claims, these terms do not represent any order or importance, and are intended to distinguish one configuration from another configuration. In the drawings, some of the members that are not important for describing the embodiments are omitted.

Embodiment 1

FIG. 1 is a schematic diagram of a hydrocarbon production apparatus 1 according to Embodiment 1. The hydrocarbon production apparatus 1 includes a synthesis gas production unit 2, a hydrocarbon production unit 4, a first separator 6, a second separator 8, and a third separator 10. The synthesis gas production unit 2 is disposed upstream of the hydrocarbon production unit 4. The second separator 8 is disposed between the synthesis gas production unit 2 and the hydrocarbon production unit 4. The first separator 6 is disposed downstream of the hydrocarbon production unit 4. The third separator 10 is disposed between the first separator 6 and the synthesis gas production unit 2. The third separator 10 is connected to the second separator 8.

The synthesis gas production unit 2 receives supply of carbon dioxide and hydrogen as feed gases. A synthesis gas containing carbon monoxide and hydrogen is produced by using the carbon dioxide and the hydrogen. Oxygen is also supplied to the synthesis gas production unit 2, and the oxygen is also used for production of the synthesis gas.

As an example, the synthesis gas production unit 2 of the present embodiment receives supply of hydrogen and oxygen from a water electrolysis module 12. In FIG. 1, the water electrolysis module 12 is illustrated as an external device with respect to the hydrocarbon production apparatus 1, but the water electrolysis module 12 may be incorporated in the hydrocarbon production apparatus 1.

The water electrolysis module 12 is an electrolyzer that generates hydrogen and oxygen by electrolysis of water. As an example, the water electrolysis module 12 has a structure in which an oxygen generating electrode having a catalyst such as iridium or platinum and a hydrogen generating electrode having a catalyst such as platinum are separated from each other by a membrane having proton conductivity. That is, the water electrolysis module 12 is a solid polymer water electrolysis module. Other examples of the water electrolysis module 12 include alkaline water electrolysis module and a solid oxide water electrolysis module. The reactions during water electrolysis in the solid polymer water electrolysis module are as shown in the following Formulas (1) and (2).

$$\text{Reaction taking place at the oxygen generating electrode:}$$
$$2H_2O \rightarrow O_2 + 4H^+ + 4e^- \tag{1}$$

$$\text{Reaction taking place at the hydrogen generating electrode:}$$
$$4H^+ + 4e^- \rightarrow 2H_2 \tag{2}$$

The water electrolysis module 12 receives supply of electric power necessary for water electrolysis from a power supply device (not illustrated). Examples of the power supply device include a power generation device that generates power using renewable energy, such as a wind power generation device or a solar power generation device. As a result, it is possible to reduce the emission amount of carbon dioxide associated with the generation of hydrogen and the production of a hydrocarbon having 5 or more carbon atoms (hereinafter, appropriately referred to as "C5+ component") as a target product. The power supply device is not limited to a power generation device using renewable energy, and may be a system power supply, a power storage device storing electric power from the renewable energy power generation device or the system power supply, or the like. A combination of two or more of these devices may be used.

As the carbon dioxide supplied to the synthesis gas production unit 2, for example, carbon dioxide recovered from the atmosphere by direct air capture (DAC) can be used. Carbon dioxide separated and recovered from combustion exhaust gas discharged from thermal power generation, a chemical plant, or the like by, for example, a chemical absorption method, a physical absorption method, or the like can be used. As a result, reduction of carbon dioxide in the atmosphere can be expected. The consumption of fossil fuel can be reduced.

In the synthesis gas production unit 2, reactions shown in the following Formulas (3) to (5) occur to produce a synthesis gas containing at least carbon monoxide and hydrogen is produced.

$$H_2 + 1/2O_2 \longrightarrow H_2O \tag{3}$$

$$CO_2 + H_2 \Longleftrightarrow CO + H_2O \tag{4}$$

$$CO_2 + 3H_2 \Longleftrightarrow CH_4 + H_2O \tag{5}$$

First, the reaction shown in Formula (3) occurs, and hydrogen contained in the feed gas is oxidized to produce water. The reaction shown in Formula (4) occurs, and carbon dioxide and hydrogen contained in the feed gas react to produce carbon monoxide and water. The reaction shown in Formula (3) is an exothermic reaction. On the other hand, the reaction shown in Formula (4) is an endothermic reaction. Heat necessary for the reaction shown in Formula (4) is covered by heat generated by the reaction shown in Formula (3). That is, the synthesis gas production unit 2 generates carbon monoxide from carbon dioxide contained in the feed gas by utilizing heat generation associated with oxidation of hydrogen contained in the feed gas.

As described above, by covering reaction heat necessary for generation of carbon monoxide by the oxidation of hydrogen, generation of soot and coking in the catalyst can be suppressed as compared with a conventional autothermal reforming reaction in which the reaction heat is covered by partial oxidation of methane. As a result, it is possible to reduce the requirement for the mixing property of the feed gas and the setting of the optimum air-fuel ratio. It is possible to suppress the deactivation of the catalyst and extend the use period of the catalyst. Therefore, the production efficiency of the C5+ component can be improved.

As shown in Formula (5), a part of carbon monoxide may react with hydrogen to generate methane and water. Therefore, methane may also be contained in the synthesis gas, in addition to hydrogen and carbon monoxide. This methanation of carbon monoxide can be suppressed by temperature control or the like of the synthesis gas production unit 2. Unreacted carbon dioxide may also be contained in the synthesis gas.

The synthesis gas discharged from the synthesis gas production unit 2 is sent to the second separator 8. The water discharged from the synthesis gas production unit 2 may be separated from the synthesis gas and supplied to, for example, the water electrolysis module 12 or the like.

The second separator 8 separates carbon dioxide from the synthesis gas. A known carbon dioxide separator can be used for the second separator 8. The carbon dioxide separated by the second separator 8 is supplied to the synthesis gas production unit 2. The synthesis gas production unit 2 receives supply of the carbon dioxide separated by the second separator 8 and also uses the carbon dioxide for production of the synthesis gas. As a result, the utilization factor of carbon dioxide is improved. Therefore, the production efficiency of the C5+ component can be improved.

The synthesis gas from which carbon dioxide is separated by the second separator 8 is sent to the hydrocarbon production unit 4. The $H_2/CO$ ratio of the synthesis gas supplied to the hydrocarbon production unit 4 is, for example, 1.80 to 2.30, preferably 1.90 to 2.20, and more preferably 2.00 to 2.10. The hydrocarbon production unit 4 produces a C5+ component as a target product by using the supplied synthesis gas. The C5+ component is, for example, normal paraffin having 5 or more carbon atoms.

The hydrocarbon production unit 4 of the present embodiment is constituted by a known FT reactor. As the FT reactor, a tubular fixed bed reactor, a slurry bed reactor, or the like can be used. In the hydrocarbon production unit 4, the reaction shown in the following Formula (6) occurs, and a C5+ component is generated by carbon-carbon chain growth. As a catalyst for FT reaction, a cobalt catalyst, a precipitated iron catalyst, a ruthenium catalyst, or the like can be used. The proportion of a reaction intermediate having n carbon atoms to be heavy into a reaction intermediate having n+1 carbon atoms by carbon-carbon chain growth is represented by a chain growth probability α. A higher α means that a higher molecular weight hydrocarbon is obtained. α varies depending on the type of catalyst and reaction conditions, and is preferably 0.75 to 0.95 and more preferably 0.85 to 0.95. In Formula (6), for example, when a is 0.95, n of the C5+ component contained in an amount of 0.1 mol % or more is, for example, an integer of 5 to 60. In the hydrocarbon production unit 4, a gaseous light hydrocarbon having 4 or less carbon atoms at normal temperature and normal pressure (hereinafter, appropriately referred to as "C4− component") such as methane, ethane, propane, and butane are also produced as by-products.

$$nCO + (2n + 1) H_2 \rightarrow C_nH_{2n+2} + nH_2O \tag{6}$$

An effluent from the hydrocarbon production unit 4 is sent to the first separator 6. The effluent may contain not only a C5+ component and a C4− component, but also water as other by-products, unreacted hydrogen, carbon monoxide, carbon dioxide, and the like. The first separator 6 can be constituted by a known gas-liquid separator, and separates the effluent into a liquid component and a gas component. The liquid component contains a C5+ component and water. The gas component contains hydrogen, carbon monoxide, carbon dioxide, and a C4− component. The gas component may contain a gaseous C5+ component.

The liquid component is separated into a C5+ component and water by a known oil-water separator (not illustrated). The separated C5+ component undergoes an upgrade treatment such as a hydrogenation treatment as necessary, and becomes a hydrocarbon product that can be used as a substitute for, for example, kerosene, gas oil, or the like. The separated water may be supplied to, for example, the water electrolysis module 12 or the like.

The gas component is sent as the recycle gas to the synthesis gas production unit 2. In the present embodiment, hydrogen, carbon monoxide, and carbon dioxide are separated from the recycle gas by the third separator 10 provided between the first separator 6 and the synthesis gas production unit 2. A known gas separator can be used for the third separator 10. As an example, the third separator 10 performs separation by using at least one of a pressure swing adsorption (PSA) method and a membrane separation method. When the third separator 10 uses a membrane separation method, as an example, the third separator 10 includes at least one of a polyimide film, a carbon film obtained by carbonizing the polyimide film, and a metal film containing Pd. The separated hydrogen, carbon monoxide, and carbon dioxide are supplied to the second separator 8.

The second separator 8 separates carbon dioxide from hydrogen, carbon monoxide, and carbon dioxide supplied from the third separator 10. Therefore, the gas supplied from the third separator 10 is separated into hydrogen and carbon monoxide, and carbon dioxide. The carbon dioxide separated by the second separator 8 is supplied to the synthesis gas production unit 2. The synthesis gas production unit 2 also uses the carbon dioxide for production of the synthesis gas. As a result, the utilization factor of carbon dioxide is improved.

The carbon monoxide and hydrogen separated by the second separator 8 are supplied to the hydrocarbon production unit 4. The hydrocarbon production unit 4 also uses the hydrogen and the carbon monoxide for production of the C5+ component. As a result, the utilization factor of hydrogen and carbon monoxide is improved. The $H_2/CO$ ratio of the synthesis gas supplied to the hydrocarbon production unit 4 can be adjusted to a value suitable for the FT reaction. Therefore, the production efficiency of the C5+ component can be improved.

The recycle gas from which hydrogen, carbon monoxide, and carbon dioxide are separated is sent to the synthesis gas production unit 2. Water is also supplied to the synthesis gas production unit 2, and the water is also used for production of the synthesis gas. In the synthesis gas production unit 2, in addition to the reactions shown in the above Formulas (3) to (5), a reforming reaction shown in the following Formula (7) occurs, and a C4− component (denoted as $C_nH_m$ in Formula (7)) contained in the recycle gas reacts with water to generate carbon monoxide and hydrogen. In Formula (7), n is an integer of 1 to 4, and m is an integer of 4 to 10. As described above, the endothermic reaction shown in Formula (7) is covered by the heat generated by the exothermic reaction shown in Formula (3) that occurs in the same apparatus. Therefore, an autothermal reforming reaction occurs in the synthesis gas production unit 2. As the synthesis gas production unit 2, a known autothermal reforming (ATR) device capable of producing a synthesis gas can be used.

$$C_nH_m + nH_2O \rightarrow nCO + (n + m/2) H_2 \tag{7}$$

In the synthesis gas production unit 2, in addition to the reactions shown in the above Formulas (3) to (5) and (7), an exothermic reaction shown in the following Formula (8) can occur (n and m in Formula (8) are the same as those in Formula (7)). Heat necessary for the endothermic reactions shown in Formulas (4) and (7) can also be covered by the heat generated in the reaction shown in Formula (8) in addition to the heat generated in the reaction shown in Formula (3).

$$C_nH_m + (n/2)\,O_2 \rightarrow nCO + (m/2)\,H_2 \tag{8}$$

The synthesis gas production unit 2 receives supply of the recycle gas and also use the C4− component contained in the recycle gas for production of the synthesis gas. As a result, the utilization factor of the C4− component is improved. By supplying the recycle gas from which hydrogen, carbon monoxide, and carbon dioxide are separated by the third separator 10 to the synthesis gas production unit 2, the energy required for raising the temperature of the synthesis gas production unit 2 to a temperature suitable for the reaction in the synthesis gas production unit 2 can be reduced. Therefore, the production efficiency of the C5+ component can be improved.

Embodiment 2

Figure 2:
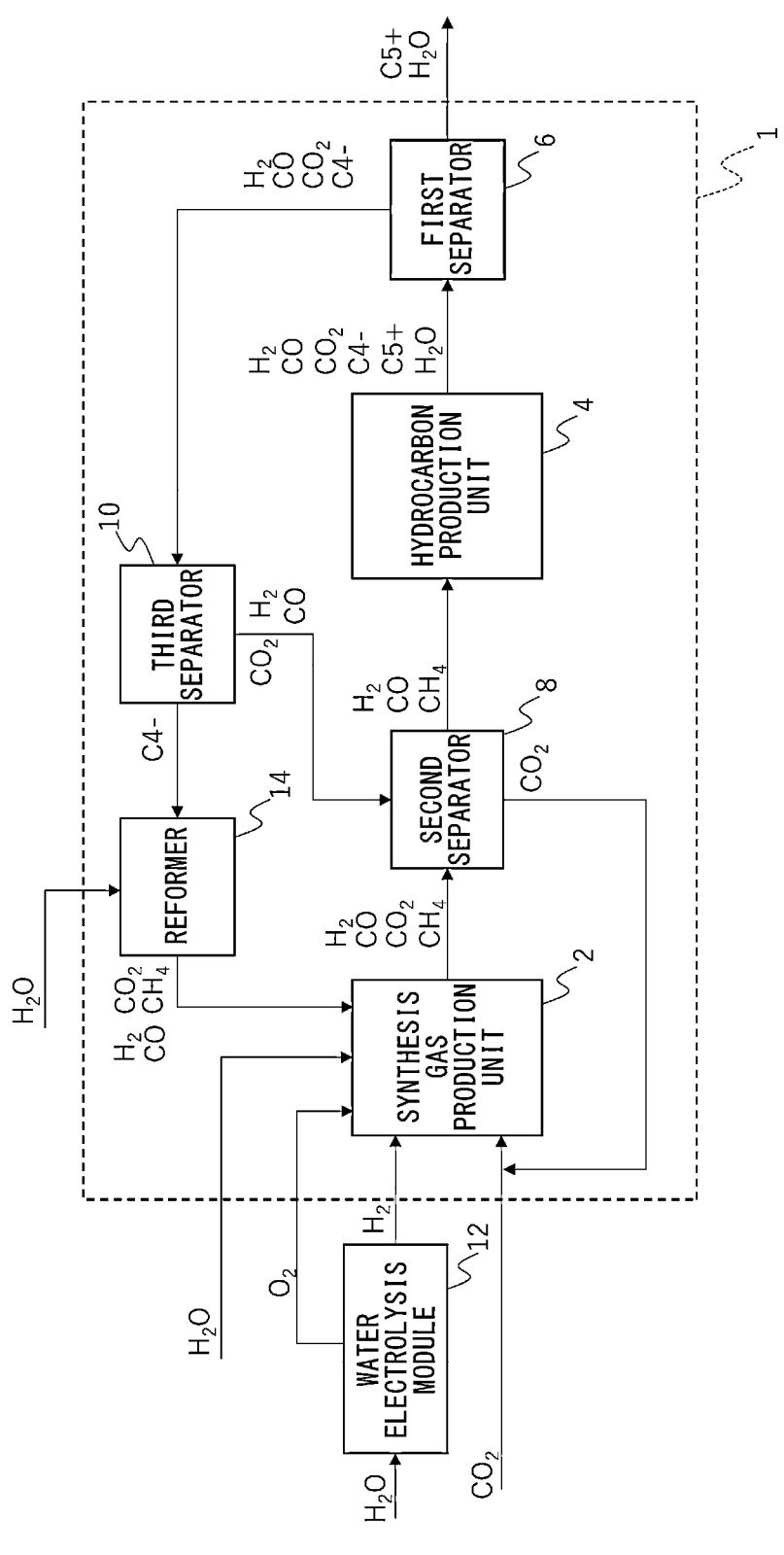
FIG. 2 is a schematic diagram of a hydrocarbon production apparatus according to Embodiment 2.

The present embodiment has a configuration common to Embodiment 1 except that the hydrocarbon production apparatus 1 includes a reformer 14. Hereinafter, the present embodiment will be described focusing on a configuration different from that of Embodiment 1, and description of common configurations will be omitted. FIG. 2 is a schematic diagram of a hydrocarbon production apparatus 1 according to Embodiment 2.

The hydrocarbon production apparatus 1 of the present embodiment includes the reformer 14 between the third separator 10 and the synthesis gas production unit 2. The recycle gas from which hydrogen, carbon monoxide, and carbon dioxide are separated by the third separator 10 is sent to the reformer 14. In the reformer 14, reactions of Formulas (9) and (10) described below occur, and the C4− component contained in the recycle gas is reformed into methane. In Formula (9), n is an integer of 1 to 4, and m is an integer of 4 to 10. By providing the reformer 14, it is possible to reduce the possibility of occurrence of catalyst deactivation and blockage of the reaction device in the synthesis gas production unit 2. The reaction of Formula (9) is a reaction for reforming the C4− component into carbon monoxide. The reaction of Formula (10) is an equilibrium reaction. In the reformer 14, an equilibrium reaction shown in Formula (11) described below also occurs. Therefore, the gas generated in the reformer 14 may contain carbon monoxide, carbon dioxide, hydrogen, and water in addition to methane.

As the reformer 14, a known reformer capable of reforming the C4− component into methane can be used. For example, a steam reformer can be used as the reformer 14. Water necessary for the reaction in the reformer 14 is supplied from the outside, for example. Water generated in the synthesis gas production unit 2 or the hydrocarbon production unit 4 may be recycled and supplied to the reformer 14. The reaction temperature of the reformer 14 is, for example, 450° C. to 600° C. and preferably 450° C. to 500° C. By treating the C4− component at 450° C. to 600° C., deposition of carbon (coke) can be suppressed. As a result, it is possible to reduce the possibility of occurrence of catalyst deactivation and blockage of the reaction device in the reformer 14.

$$C_nH_m + nH_2O \rightarrow nCO + (n + m/2)\,H_2 \tag{9}$$

$$CO + 3H_2 \Longleftrightarrow CH_4 + H_2O \tag{10}$$

$$CO + H_2O \Longleftrightarrow CO_2 + H_2 \tag{11}$$

The recycle gas containing methane generated by the reformer 14 is sent to the synthesis gas production unit 2. The synthesis gas production unit 2 receives supply of the recycle gas and also uses methane, hydrogen, carbon monoxide, and carbon dioxide contained in the recycle gas for production of the synthesis gas. By reforming the C4-component in the recycle gas into methane, hydrogen, carbon monoxide, and carbon dioxide and supplying those components to the synthesis gas production unit 2, the composition of the synthesis gas can be easily adjusted to a composition suitable for the reaction in the hydrocarbon production unit 4. Therefore, the production efficiency of the C5+ component can be improved.

The reformer 14 may be capable of performing a dry reforming reaction shown in the following Formula (12).

$$CH_4 + CO_2 \Longleftrightarrow 2H_2 + 2CO \tag{12}$$

Embodiment 1 and Embodiment 2 can include the following modifications.

Modification 1

The hydrocarbon production apparatus 1 may not include the third separator 10. In this case, the recycle gas containing hydrogen, carbon monoxide, carbon dioxide, and a C4− component or methane is supplied to the synthesis gas production unit 2.

Modification 2

Figure 3:
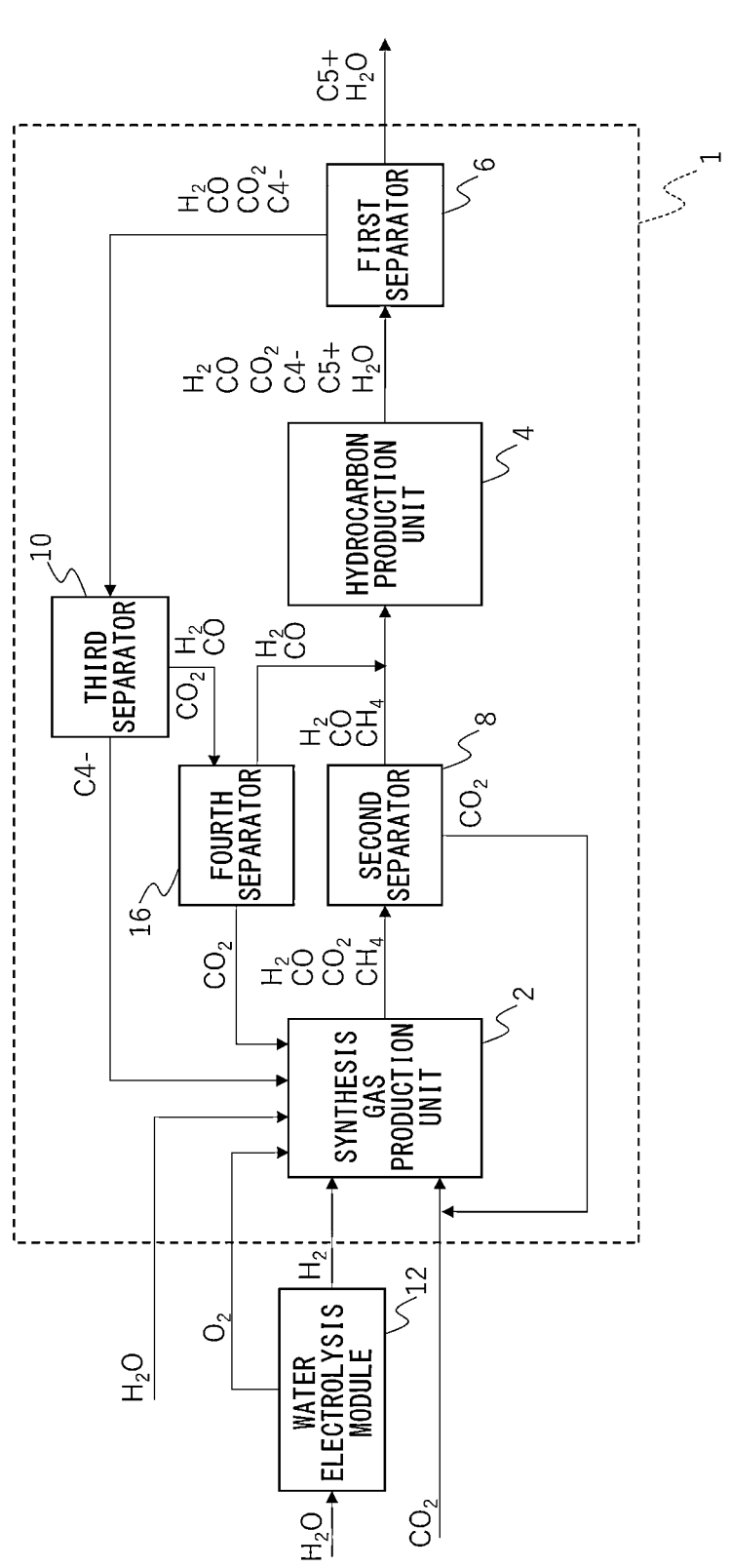
FIG. 3 is a schematic diagram of a hydrocarbon production apparatus according to Modification 2.

FIG. 3 is a schematic diagram of a hydrocarbon production apparatus 1 according to Modification 2. Although FIG. 3 illustrates a structure in which a fourth separator 16 is added to the hydrocarbon production apparatus 1 of Embodiment 1, the fourth separator 16 can also be added to the hydrocarbon production apparatus 1 of Embodiment 2.

The hydrocarbon production apparatus 1 may include the fourth separator 16 that receives supply of hydrogen, carbon monoxide, and carbon dioxide from the third separator 10 instead of the second separator 8. The fourth separator 16 separates hydrogen, carbon monoxide, and carbon dioxide supplied from the third separator 10 into hydrogen and carbon monoxide, and carbon dioxide. A known carbon dioxide separator can be used for the fourth separator 16, similarly to the second separator 8. The carbon dioxide separated by the fourth separator 16 may be supplied to the synthesis gas production unit 2. When the reformer 14 performs the dry reforming reaction shown in the above Formula (12), the carbon dioxide separated by the fourth separator 16 may be supplied to the reformer 14. The hydrogen and carbon monoxide separated by the fourth separator 16 are supplied to the hydrocarbon production unit 4. The hydrocarbon production unit 4 also uses the hydrogen and the carbon monoxide for production of the C5+ component.

Modification 3

The hydrocarbon production unit 4 may be constituted by a known methanol synthesizer and a known methanol-gasoline reactor (hereinafter, appropriately referred to as "MTG reactor") instead of the FT reactor. First, a reaction shown in the following Formula (13) occurs in the methanol synthesizer, and methanol is synthesized from a synthesis gas containing hydrogen and carbon monoxide. Reactions shown in the following Formulas (14) and (15) then occur in the MTG reactor to obtain a hydrocarbon (in Formula (15), as an example, a lower olefin having one double bond and n carbon atoms is denoted as $C_nH_{2n}$) as a target product from methanol. In Formula (15), n is, for example, an integer of 2 to 10. The obtained hydrocarbon contains olefin, paraffin, aroma (aromatic hydrocarbon), naphthene, and the like.

$$CO + 2H_2 \rightarrow CH_3OH \tag{13}$$

$$CH_3OH \rightarrow 1/2CH_3—O—CH_3 + 1/2H_2O \tag{14}$$

$$n/2CH_3—O—CH_3 \longrightarrow C_nH_{2n} + n/2H_2O \tag{15}$$

Modification 4

The hydrocarbon production unit 4 may be constituted by a known syngas-olefin reactor (hereinafter, appropriately referred to as "STO reactor") instead of the FT reactor. A reaction shown in the following Formula (16) occurs in the STO reactor to obtain a hydrocarbon as a target product from a synthesis gas containing hydrogen and carbon monoxide. The obtained hydrocarbon mainly contains a lower olefin (in Formula (16), a lower olefin having one double bond and n carbon atoms is denoted as $C_nH_{2n}$). In Formula (16), n is, for example, an integer of 2 to 10.

$$nCO + 2nH_2 \rightarrow C_nH_{2n} + nH_2O \tag{16}$$

Embodiment 3

Figure 4:
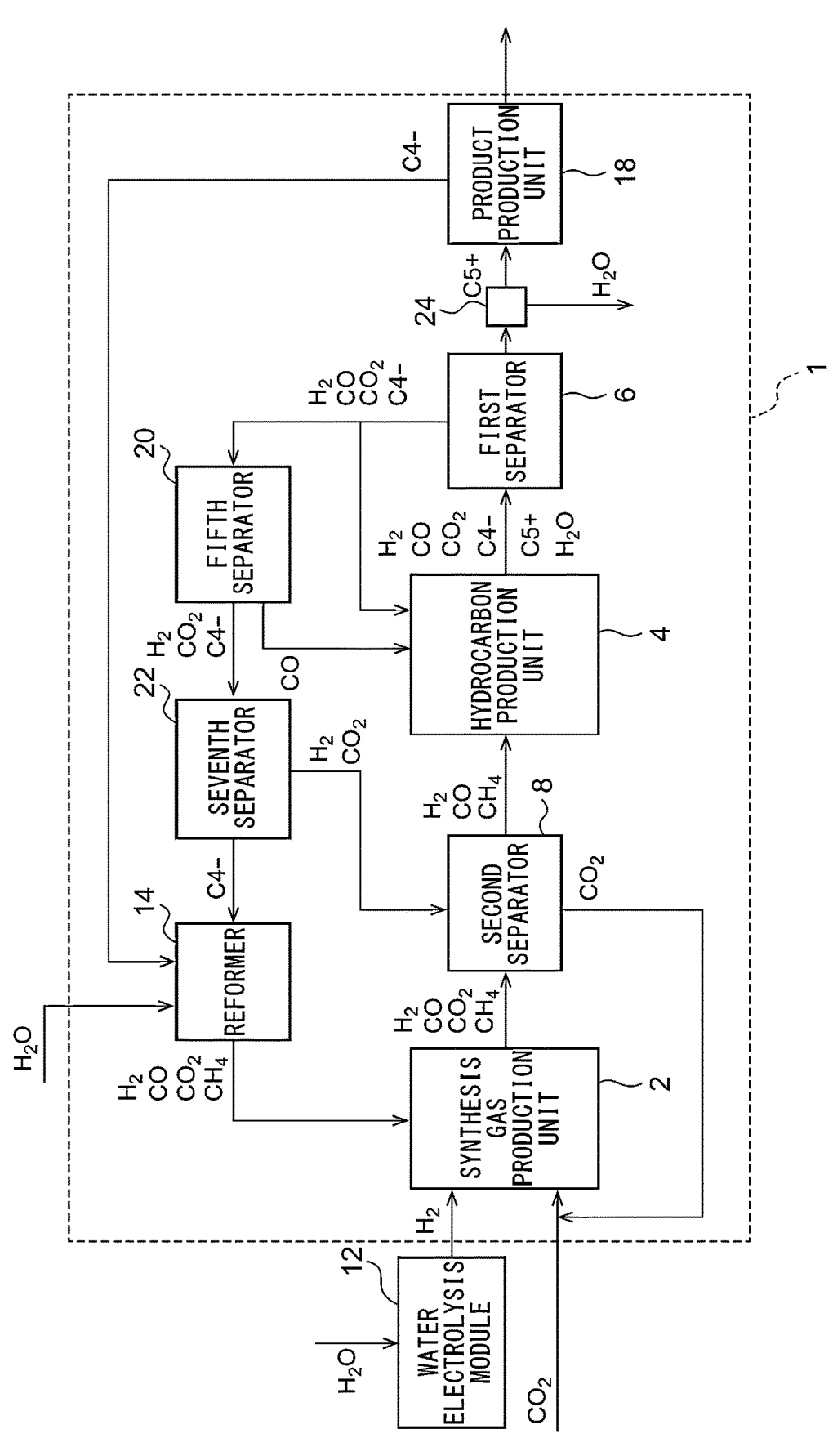
FIG. 4 is a schematic diagram of a hydrocarbon production apparatus according to Embodiment 3.

The present embodiment has a configuration common to Embodiment 1 except for a part of the structure of the hydrocarbon production apparatus 1. Hereinafter, the present embodiment will be described focusing on a configuration different from that of Embodiment 1, and description of common configurations will be omitted. FIG. 4 is a schematic diagram of a hydrocarbon production apparatus 1 according to Embodiment 3.

The hydrocarbon production apparatus 1 includes a synthesis gas production unit 2, a hydrocarbon production unit 4, a first separator 6, a second separator 8, a product production unit 18, a fifth separator 20, a seventh separator 22, and a reformer 14. The synthesis gas production unit 2 is disposed upstream of the hydrocarbon production unit 4. The second separator 8 is disposed between the synthesis gas production unit 2 and the hydrocarbon production unit 4.

The first separator 6 is disposed downstream of the hydrocarbon production unit 4. The product production unit 18 is disposed downstream of the first separator 6. The fifth separator 20, the seventh separator 22, and the reformer 14 are disposed between the first separator 6 and the synthesis gas production unit 2. The fifth separator 20 is connected to the hydrocarbon production unit 4, and the seventh separator 22 is connected to the second separator 8.

The synthesis gas production unit 2 produces a synthesis gas containing carbon monoxide and hydrogen by using carbon dioxide and hydrogen. As an example, the synthesis gas production unit 2 receives supply of hydrogen from a water electrolysis module 12. In the synthesis gas production unit 2, the reverse shift reaction represented by the above Formula (4) occurs to produce a synthesis gas containing at least carbon monoxide and hydrogen is produced. Heat necessary for the reverse shift reaction is supplied from the outside, for example. As shown in the above Formula (5), a part of carbon monoxide may react with hydrogen to generate methane and water. Therefore, methane may also be contained in the synthesis gas, in addition to hydrogen and carbon monoxide. Unreacted carbon dioxide may also be contained in the synthesis gas. The synthesis gas discharged from the synthesis gas production unit 2 is sent to the second separator 8.

The second separator 8 separates carbon dioxide from the synthesis gas. The carbon dioxide separated by the second separator 8 is supplied to the synthesis gas production unit 2. The synthesis gas production unit 2 receives supply of the carbon dioxide separated by the second separator 8 and also uses the carbon dioxide for production of the synthesis gas. The synthesis gas from which carbon dioxide is separated by the second separator 8 is sent to the hydrocarbon production unit 4. The hydrocarbon production unit 4 produces a C5+ component by using the supplied synthesis gas. In the hydrocarbon production unit 4, the reaction shown in the above Formula (6) occurs, and a C5+ component is generated by carbon-carbon chain growth. In the hydrocarbon production unit 4, a C4− component is also by-produced.

An effluent from the hydrocarbon production unit 4 is sent to the first separator 6. The first separator 6 can be constituted by a known gas-liquid separator, and separates the effluent into a liquid component and a gas component. The liquid component contains a C5+ component and water. The gas component contains hydrogen, carbon monoxide, carbon dioxide, and a C4− component.

The liquid component is separated into a C5+ component and water by a known oil-water separator 24. The separated C5+ component is sent to the product production unit 18. The product production unit 18 performs an upgrade treatment such as a hydrogenation treatment on the C5+ component supplied from the hydrocarbon production unit 4 to produce a hydrocarbon product that can be used as a substitute for kerosene, gas oil, or the like. The product production unit 18 by-produces a C4− component together with the hydrocarbon product.

The gas component is used as the recycle gas. In the present embodiment, a part of the recycle gas is directly returned from the first separator 6 to the hydrocarbon production unit 4. The hydrocarbon production unit 4 receives supply of the part of the recycle gas from the first separator 6 and also uses the recycle gas for production of the C5+ component. The conversion of carbon monoxide in one reaction in the hydrocarbon production unit 4, that is, when the synthesis gas is passed through the hydrocarbon production unit 4 once is, for example, about 50 to 60%. By returning the part of the recycle gas from the first separator 6 to the hydrocarbon production unit 4, the conversion can be increased to, for example, about 80 to 99%, 85% to 97%, or 90% to 95%. By returning the part of the recycle gas directly from the first separator 6 to the hydrocarbon production unit 4, a load applied to the fifth separator 20 and the seventh separator 22 can be reduced, and an increase in facility scale of these separators can be suppressed. An increase in facility scale of the synthesis gas production unit 2, the second separator 8, the reformer 14, and the like to which the separated recycle gas is supplied can be suppressed. Therefore, the process efficiency in the hydrocarbon production apparatus 1 can be improved.

The remaining recycle gas flowing out of the first separator 6 is sent to the fifth separator 20 provided between the first separator 6 and the synthesis gas production unit 2. The fifth separator 20 separates carbon monoxide from the recycle gas. As the fifth separator 20, for example, a known separator that separates carbon monoxide by a PSA method can be used. The carbon monoxide separated by the fifth separator 20 is supplied to the hydrocarbon production unit 4. The hydrocarbon production unit 4 also uses the carbon monoxide for production of the C5+ component. As a result, the utilization factor of carbon monoxide is improved, and the production efficiency of the C5+ component is improved. By separation of carbon monoxide by the fifth separator 20, a load applied to the seventh separator 22 can be reduced, and an increase in facility scale of the seventh separator 22 can be suppressed. An increase in facility scale of the synthesis gas production unit 2, the second separator 8, the reformer 14, and the like to which the separated recycle gas is supplied can be suppressed. Therefore, the process efficiency in the hydrocarbon production apparatus 1 can be improved.

The recycle gas from which carbon monoxide is separated by the fifth separator 20 is sent to the seventh separator 22 provided between the fifth separator 20 and the synthesis gas production unit 2. The seventh separator 22 separates hydrogen and carbon dioxide from the recycle gas supplied from the fifth separator 20. As the seventh separator 22, for example, a known separator that separates hydrogen and carbon dioxide by a membrane separation method can be used. The hydrogen and carbon dioxide separated by the seventh separator 22 are supplied to the second separator 8. As a result, the utilization factor of hydrogen and carbon dioxide is improved, and the production efficiency of the C5+ component is improved. By separation of hydrogen and carbon dioxide by the seventh separator 22, a load applied to the reformer 14 can be reduced, and an increase in facility scale can be suppressed. Therefore, the process efficiency in the hydrocarbon production apparatus 1 can be improved.

The second separator 8 separates hydrogen and carbon dioxide supplied from the seventh separator 22 into hydrogen and carbon dioxide. The hydrogen separated by the second separator 8 is supplied to the hydrocarbon production unit 4. The hydrocarbon production unit 4 also uses the hydrogen for production of the C5+ component. As a result, the utilization factor of hydrogen is improved, and the production efficiency of the C5+ component is improved. The carbon dioxide separated by the second separator 8 is supplied to the synthesis gas production unit 2. The synthesis gas production unit 2 also uses the carbon dioxide for production of the synthesis gas. As a result, the utilization factor of carbon dioxide is improved, and the production efficiency of the C5+ component is improved.

The recycle gas from which hydrogen and carbon dioxide are separated by the seventh separator 22 is sent to the reformer 14 provided between the seventh separator 22 and the synthesis gas production unit 2. In the reformer 14, the reactions of the above Formulas (9), (10), and (11) occur, and the C4− component contained in the recycle gas is reformed into methane, hydrogen, carbon monoxide, and carbon dioxide. The recycle gas containing methane, hydrogen, carbon monoxide, and carbon dioxide generated by the reformer 14 is sent to the synthesis gas production unit 2. The synthesis gas production unit 2 receives supply of the recycle gas and also uses methane, hydrogen, carbon monoxide, and carbon dioxide contained in the recycle gas for production of the synthesis gas. When the reaction temperature of the synthesis gas production unit 2 is set to 700° C. or higher, preferably 800° C. or higher, and more preferably 1000° C. or higher, a synthesis gas can be efficiently produced from methane and water by the reverse reaction of the reaction shown in the above Formula (5). As a result, the utilization factor of the C4− component is improved, and the production efficiency of the C5+ component is improved.

The C4− component by-produced by the product production unit 18 is supplied to the reformer 14. The reformer 14 also reforms the C4− component into methane, hydrogen, carbon monoxide, and carbon dioxide. As a result, the utilization factor of the C4− component is improved, and the production efficiency of the C5+ component is improved.

Modification 5

Figure 5:
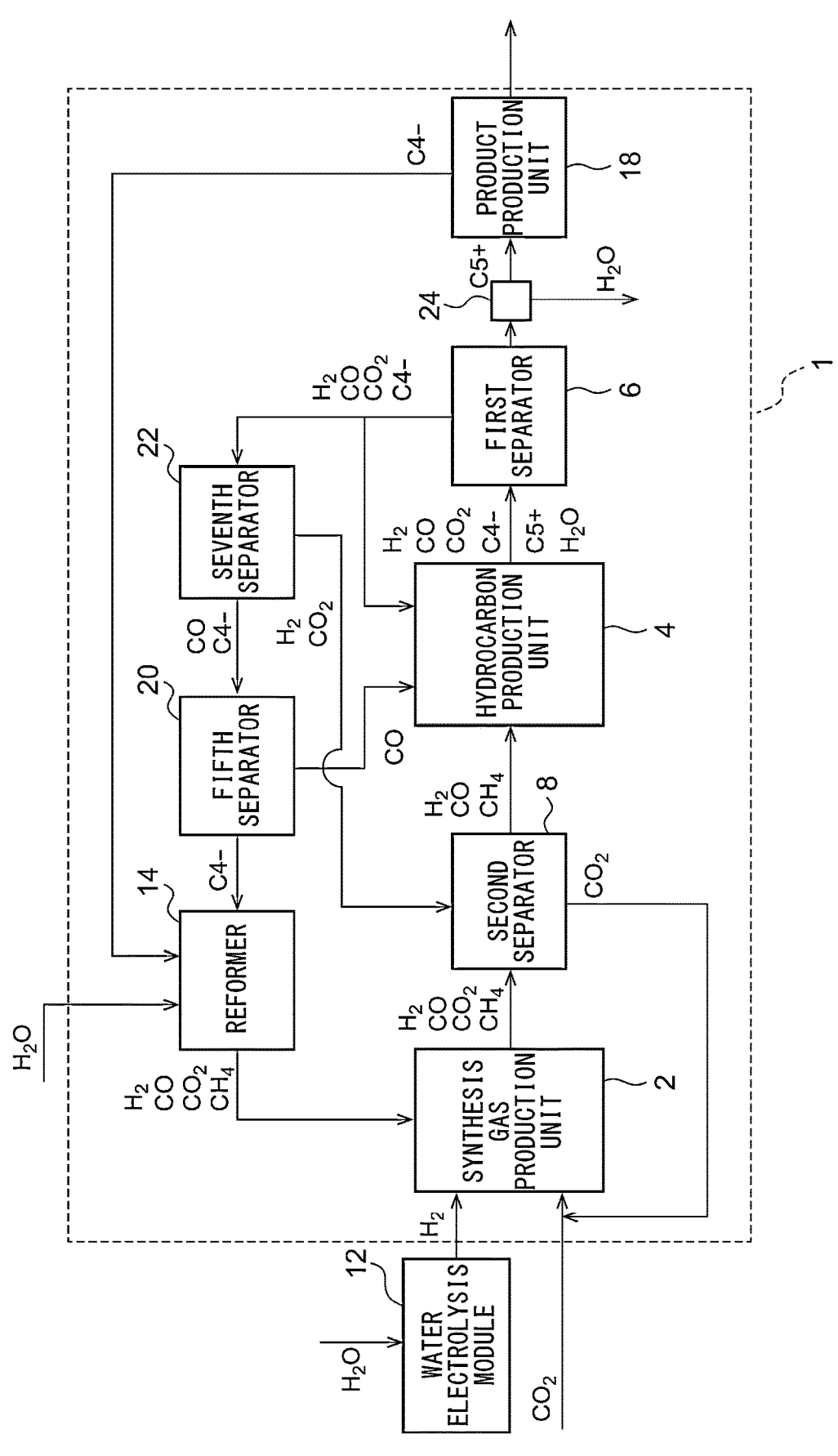
FIG. 5 is a schematic diagram of a hydrocarbon production apparatus according to Modification 5.

Embodiment 3 can include Modification 5. FIG. 5 is a schematic diagram of a hydrocarbon production apparatus 1 according to Modification 5. The present modification has a configuration common to Embodiment 3 except that the arrangement of the fifth separator 20 and the seventh separator 22 is reversed.

A part of the recycle gas flowing out of the first separator 6 is directly returned from the first separator 6 to the hydrocarbon production unit 4. The hydrocarbon production unit 4 receives supply of the part of the recycle gas from the first separator 6 and also uses the recycle gas for production of the C5+ component. The remaining recycle gas is sent to the seventh separator 22 provided between the first separator 6 and the synthesis gas production unit 2. The seventh separator 22 separates hydrogen and carbon dioxide from the recycle gas. The hydrogen and carbon dioxide separated by the seventh separator 22 are supplied to the second separator 8. In the seventh separator 22, a part of carbon monoxide in the recycle gas can also be separated.

The second separator 8 separates hydrogen and carbon dioxide supplied from the seventh separator 22 into hydrogen and carbon dioxide. The hydrogen separated by the second separator 8 is supplied to the hydrocarbon production unit 4. The hydrocarbon production unit 4 also uses the hydrogen for production of the C5+ component. The carbon dioxide separated by the second separator 8 is supplied to the synthesis gas production unit 2. The synthesis gas production unit 2 also uses the carbon dioxide for production of the synthesis gas.

The recycle gas from which hydrogen and carbon dioxide are separated by the seventh separator 22 is sent to the fifth separator 20 provided between the seventh separator 22 and the synthesis gas production unit 2. The fifth separator 20 separates carbon monoxide from the recycle gas supplied from the seventh separator 22. The carbon monoxide separated by the fifth separator 20 is supplied to the hydrocarbon production unit 4. The hydrocarbon production unit 4 also uses the carbon monoxide for production of the C5+ component.

The recycle gas from which carbon monoxide is separated by the fifth separator 20 is sent to the reformer 14 provided between the fifth separator 20 and the synthesis gas production unit 2. The reformer 14 reforms the C4-component contained in the recycle gas into methane, hydrogen, carbon monoxide, and carbon dioxide. The C4-component by-produced by the product production unit 18 is supplied to the reformer 14. The reformer 14 also reforms the C4– component into methane, hydrogen, carbon monoxide, and carbon dioxide. The recycle gas containing methane, hydrogen, carbon monoxide, and carbon dioxide generated by the reformer 14 is sent to the synthesis gas production unit 2. The synthesis gas production unit 2 also uses methane, hydrogen, carbon monoxide, and carbon dioxide contained in the recycle gas for production of the synthesis gas. When the reaction temperature of the synthesis gas production unit 2 is set to 700° C. or higher, preferably 800° C. or higher, and more preferably 1000° C. or higher, a synthesis gas can be efficiently produced from methane and water by the reverse reaction of the reaction shown in the above Formula (5).

Embodiment 4

Figure 6:
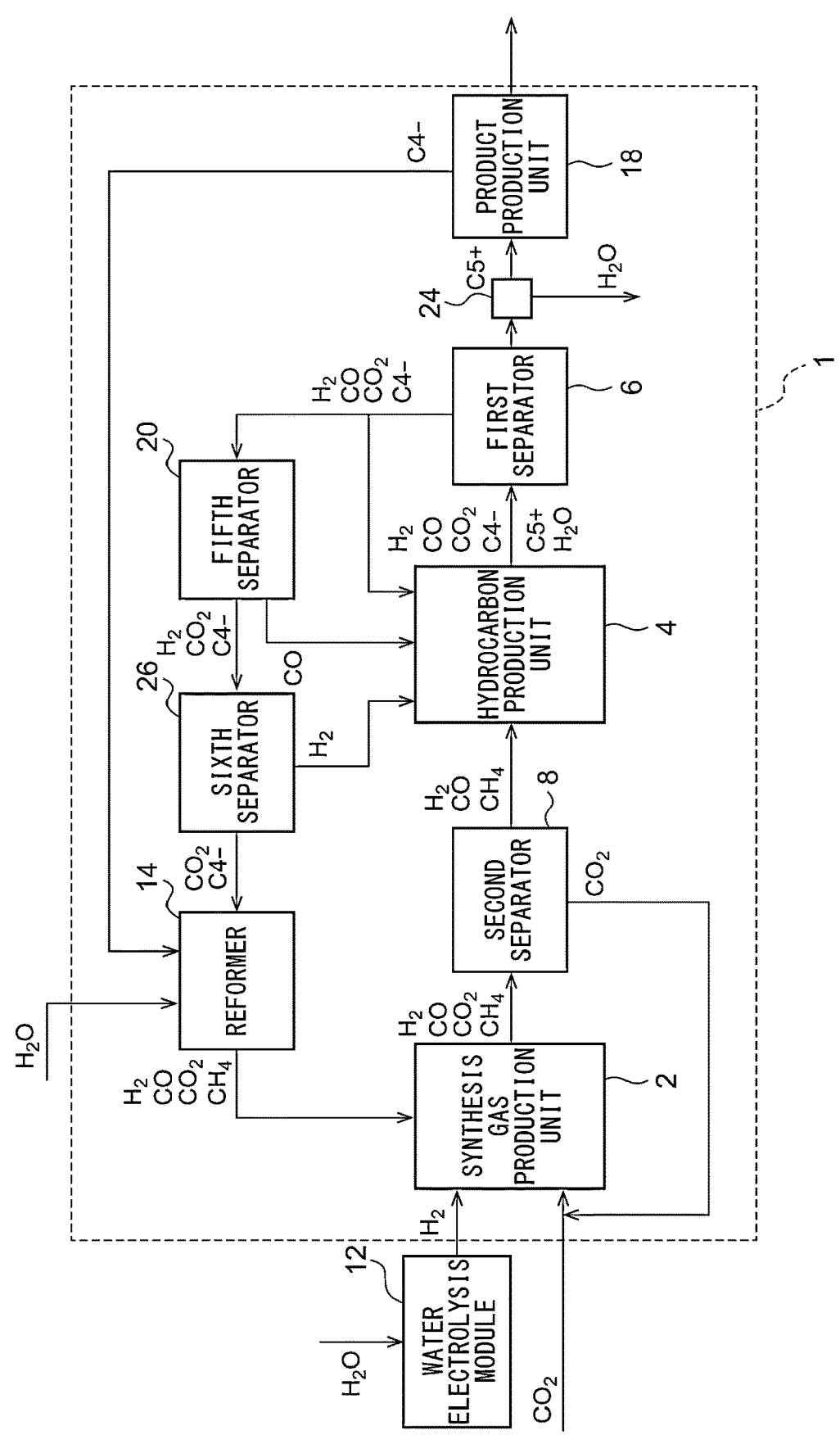
FIG. 6 is a schematic diagram of a hydrocarbon production apparatus according to Embodiment 4.

The present embodiment has a configuration common to Embodiment 3 except for a part of the structure of the hydrocarbon production apparatus 1. Hereinafter, the present embodiment will be described focusing on a configuration different from that of Embodiment 3, and description of common configurations will be omitted. FIG. 6 is a schematic diagram of a hydrocarbon production apparatus 1 according to Embodiment 4. The present embodiment is different from Embodiment 3 in that the hydrocarbon production apparatus 1 includes a sixth separator 26 instead of the seventh separator 22.

A part of the recycle gas flowing out of the first separator 6 is directly returned from the first separator 6 to the hydrocarbon production unit 4. The hydrocarbon production unit 4 receives supply of the part of the recycle gas from the first separator 6 and also uses the recycle gas for production of the C5+ component. The remaining recycle gas is sent to the fifth separator 20 provided between the first separator 6 and the synthesis gas production unit 2. The fifth separator 20 separates carbon monoxide from the recycle gas. The carbon monoxide separated by the fifth separator 20 is supplied to the hydrocarbon production unit 4. The hydrocarbon production unit 4 also uses the carbon monoxide for production of the C5+ component. By separation of carbon monoxide by the fifth separator 20, a load applied to the sixth separator 26 can be reduced, and an increase in facility scale of the sixth separator 26 can be suppressed. An increase in facility scale of the synthesis gas production unit 2, the reformer 14, and the like to which the separated recycle gas is supplied can be suppressed. Therefore, the process efficiency in the hydrocarbon production apparatus 1 can be improved.

The recycle gas from which carbon monoxide is separated by the fifth separator 20 is sent to the sixth separator 26 provided between the fifth separator 20 and the synthesis gas production unit 2. The sixth separator 26 separates hydrogen from the recycle gas supplied from the fifth separator 20. As the sixth separator 26, for example, a known separator that separates hydrogen by a PSA method, a membrane separation method, or the like can be used. The hydrogen separated by the sixth separator 26 is supplied to the hydrocarbon production unit 4. The hydrocarbon production unit 4 also uses the hydrogen for production of the C5+ component. As a result, the utilization factor of hydrogen is improved. By separation of hydrogen by the sixth separator 26, a load applied to the reformer 14 can be reduced, and an increase in facility scale can be suppressed. Therefore, the process efficiency in the hydrocarbon production apparatus 1 can be improved.

The recycle gas from which hydrogen is separated by the sixth separator 26 is sent to the reformer 14 provided between the sixth separator 26 and the synthesis gas production unit 2. The reformer 14 reforms the C4– component contained in the recycle gas into methane, hydrogen, carbon monoxide, and carbon dioxide. The C4– component by-produced by the product production unit 18 is supplied to the reformer 14. The reformer 14 also reforms the C4– component into methane, hydrogen, carbon monoxide, and carbon dioxide. The recycle gas containing methane, hydrogen, carbon monoxide, and carbon dioxide generated by the reformer 14 is sent to the synthesis gas production unit 2. The synthesis gas production unit 2 also uses methane, hydrogen, carbon monoxide, and carbon dioxide contained in the recycle gas for production of the synthesis gas. When the reaction temperature of the synthesis gas production unit 2 is set to 700° C. or higher, preferably 800° C. or higher, and more preferably 1000° C. or higher, a synthesis gas can be efficiently produced from methane and water by the reverse reaction of the reaction shown in the above Formula (5).

Modification 6

Figure 7:
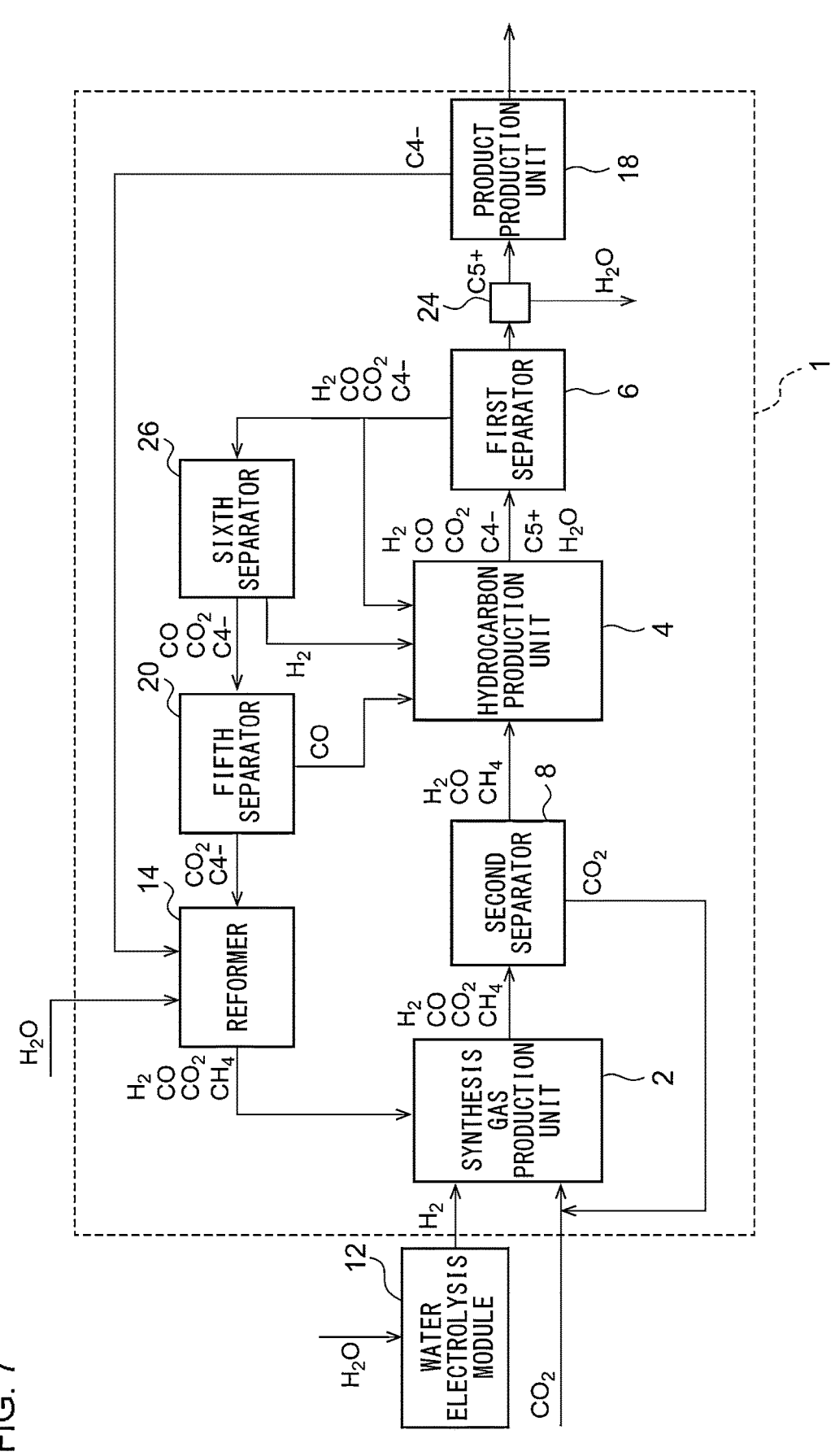
FIG. 7 is a schematic diagram of a hydrocarbon production apparatus according to Modification 6.

Embodiment 4 can include Modification 6. FIG. 7 is a schematic diagram of a hydrocarbon production apparatus 1 according to Modification 6. The present modification has a configuration common to Embodiment 4 except that the arrangement of the fifth separator 20 and the sixth separator 26 is reversed.

A part of the recycle gas flowing out of the first separator 6 is directly returned from the first separator 6 to the hydrocarbon production unit 4. The hydrocarbon production unit 4 receives supply of the part of the recycle gas from the first separator 6 and also uses the recycle gas for production of the C5+ component. The remaining recycle gas is sent to the sixth separator 26 provided between the first separator 6 and the synthesis gas production unit 2. The sixth separator 26 separates hydrogen from the recycle gas. The hydrogen separated by the sixth separator 26 is supplied to the hydrocarbon production unit 4. The hydrocarbon production unit 4 also uses the hydrogen for production of the C5+ component.

The recycle gas from which hydrogen is separated by the sixth separator 26 is sent to the fifth separator 20 provided between the sixth separator 26 and the synthesis gas production unit 2. The fifth separator 20 separates carbon monoxide from the recycle gas supplied from the sixth separator 26. The carbon monoxide separated by the fifth separator 20 is supplied to the hydrocarbon production unit 4. The hydrocarbon production unit 4 also uses the carbon monoxide for production of the C5+ component.

The recycle gas from which carbon monoxide is separated by the fifth separator 20 is sent to the reformer 14 provided between the fifth separator 20 and the synthesis gas production unit 2. The reformer 14 reforms the C4-component contained in the recycle gas into methane, hydrogen, carbon monoxide, and carbon dioxide. The C4-component by-produced by the product production unit 18 is supplied to the reformer 14. The reformer 14 also reforms the C4– component into methane, hydrogen, carbon monoxide, and carbon dioxide. The recycle gas containing methane, hydrogen, carbon monoxide, and carbon dioxide generated by the reformer 14 is sent to the synthesis gas production unit 2. The synthesis gas production unit 2 also uses methane, hydrogen, carbon monoxide, and carbon dioxide contained in the recycle gas for production of the synthesis gas. When the reaction temperature of the synthesis gas production unit 2 is set to 700° C. or higher, preferably 800° C. or higher, and more preferably 1000° C. or higher, a synthesis gas can be efficiently produced from methane and water by the reverse reaction of the reaction shown in the above Formula (5).

The present invention may be identified by the items described below.

[Item 1]

A hydrocarbon production apparatus (1) including:

a synthesis gas production unit (2) structured to produce a synthesis gas containing carbon monoxide and hydrogen by using carbon dioxide and hydrogen;

a hydrocarbon production unit (4) structured to produce a hydrocarbon (C5+) by using the synthesis gas; and a first separator (6) structured to separate a recycle gas containing a light hydrocarbon (C4–) having 4 or less carbon atoms from an effluent from the hydrocarbon production unit (4), in which the synthesis gas production unit (2) is structured to receive supply of the recycle gas and also use the recycle gas for production of the synthesis gas.

[Item 2]

The hydrocarbon production apparatus (1) described in Item 1, in which the hydrocarbon production unit (4) is structured to receive supply of a part of the recycle gas from the first separator (6) and also use the recycle gas for production of the hydrocarbon (C5+).

[Item 3]

The hydrocarbon production apparatus (1) described in Item 1 or 2, in which the synthesis gas also contains carbon dioxide, the hydrocarbon production apparatus (1) includes a second separator (8) structured to separate carbon dioxide from the synthesis gas, and the synthesis gas production unit (2) is structured to receive supply of the carbon dioxide separated by the second separator (8) and also use the carbon dioxide for production of the synthesis gas.

[Item 4]

The hydrocarbon production apparatus (1) described in any one of Items 1 to 3, in which the recycle gas also contains carbon monoxide, the hydrocarbon production apparatus (1) includes a fifth separator (20) structured to separate carbon monoxide from the recycle gas, and the hydrocarbon production unit (4) is structured to receive supply of the carbon monoxide separated by the fifth separator (20) and also use the carbon monoxide for production of the hydrocarbon (C5+).

[Item 5]

The hydrocarbon production apparatus (1) described in Item 3, in which the recycle gas also contains hydrogen, carbon monoxide, and carbon dioxide, the hydrocarbon production apparatus (1) includes a third separator (10) structured to separate hydrogen, carbon monoxide, and carbon dioxide from the recycle gas, the second separator (8) is structured to receive supply of hydrogen, carbon monoxide, and carbon dioxide from the third separator (10) and separate the hydrogen, the carbon monoxide, and the carbon dioxide into hydrogen and carbon monoxide, and carbon dioxide, and the hydrocarbon production unit (4) is structured to receive supply of the hydrogen and carbon monoxide separated by the second separator (8) and also use the hydrogen and carbon monoxide for production of the hydrocarbon (C5+).

[Item 6]

The hydrocarbon production apparatus (1) described in any one of Items 1 to 3, in which the recycle gas also contains hydrogen, carbon monoxide, and carbon dioxide, the hydrocarbon production apparatus (1) includes a third separator (10) structured to separate hydrogen, carbon monoxide, and carbon dioxide from the recycle gas, and a fourth separator (16) structured to receive supply of hydrogen, carbon monoxide, and carbon dioxide from the third separator (10) and separate the hydrogen, the carbon monoxide, and the carbon dioxide into hydrogen and carbon monoxide, and carbon dioxide, and the hydrocarbon production unit (4) is structured to receive supply of the hydrogen and carbon monoxide separated by the fourth separator (16) and also use the hydrogen and carbon monoxide for production of the hydrocarbon (C5+).

[Item 7]

The hydrocarbon production apparatus (1) described in any one of Items 1 to 3, in which the recycle gas also contains hydrogen, the hydrocarbon production apparatus (1) includes a sixth separator (26) structured to separate hydrogen from the recycle gas, and the hydrocarbon production unit (4) is structured to receive supply of the hydrogen separated by the sixth separator (26) and also use the hydrogen for production of the hydrocarbon (C5+).

[Item 8]

The hydrocarbon production apparatus (1) described in Item 3, in which the recycle gas also contains hydrogen, carbon monoxide, and carbon dioxide, the hydrocarbon production apparatus (1) includes a fifth separator (20) structured to separate carbon monoxide from the recycle gas, and a seventh separator (22) structured to receive supply of the recycle gas from which carbon monoxide is separated by the fifth separator (20) and separate hydrogen and carbon dioxide from the recycle gas, the second separator (8) is structured to receive supply of the hydrogen and carbon dioxide separated by the seventh separator (22) and separate the hydrogen and the carbon dioxide into hydrogen and carbon dioxide, and the hydrocarbon production unit (4) is structured to receive supply of the carbon monoxide separated by the fifth separator (20) and the hydrogen separated by the second separator (8) and also use the carbon monoxide and the hydrogen for production of the hydrocarbon (C5+).

[Item 9]

The hydrocarbon production apparatus (1) described in any one of Items 1 to 3, in which the recycle gas also contains hydrogen and carbon monoxide, the hydrocarbon production apparatus (1) includes a fifth separator (20) structured to separate carbon monoxide from the recycle gas, and a sixth separator (26) structured to receive supply of the recycle gas from which carbon monoxide is separated by the fifth separator (20) and separate hydrogen from the recycle gas, and the hydrocarbon production unit (4) is structured to receive supply of the carbon monoxide separated by the fifth separator (20) and the hydrogen separated by the sixth separator (26) and also use the carbon monoxide and the hydrogen for production of the hydrocarbon (C5+).

[Item 10]

The hydrocarbon production apparatus (1) described in Item 3, in which the recycle gas also contains hydrogen, carbon monoxide, and carbon dioxide, the hydrocarbon production apparatus (1) includes a seventh separator (22) structured to separate hydrogen and carbon dioxide from the recycle gas, and a fifth separator (20) structured to receive supply of the recycle gas from which hydrogen and carbon dioxide are separated by the seventh separator (22) and separate carbon monoxide from the recycle gas, the second separator (8) is structured to receive supply of the hydrogen and carbon dioxide separated by the seventh separator (22) and separate the hydrogen and the carbon dioxide into hydrogen and carbon dioxide, and the hydrocarbon production unit (4) is structured to receive supply of the carbon monoxide separated by the fifth separator (20) and the hydrogen separated by the second separator (8) and also use the carbon monoxide and the hydrogen for production of the hydrocarbon (C5+).

[Item 11]

The hydrocarbon production apparatus (1) described in any one of Items 1 to 3, in which the recycle gas also contains hydrogen and carbon monoxide, the hydrocarbon production apparatus (1) includes a sixth separator (26) structured to separate hydrogen from the recycle gas, and a fifth separator (20) structured to receive supply of the recycle gas from which hydrogen is separated by the sixth separator (26) and separate carbon monoxide from the recycle gas, and the hydrocarbon production unit (4) is structured to receive supply of the hydrogen separated by the sixth separator (26) and the carbon monoxide separated by the fifth separator (20) and also use the hydrogen and the carbon monoxide for production of the hydrocarbon (C5+).

[Item 12]

The hydrocarbon production apparatus (1) described in any one of Items 1 to 11, including a reformer (14) structured to reform the light hydrocarbon (C4−) into methane, in which the synthesis gas production unit (2) is structured to receive supply of the methane generated by the reformer (14) and also use the methane for production of the synthesis gas.

[Item 13]

The hydrocarbon production apparatus (1) described in Item 12, in which the hydrocarbon production apparatus (1) includes a product production unit (18) structured to receive supply of the hydrocarbon (C5+) from the hydrocarbon production unit (4) and produce a hydrocarbon product, the product production unit (18) is structured to by-produce the light hydrocarbon (C4−) together with the hydrocarbon product, and the reformer (14) is structured to receive supply of the light hydrocarbon (C4−) from the product production unit (18) and also reform the light hydrocarbon (C4−) into methane.

[Item 14]

A hydrocarbon production method including:

a synthesis gas production step of producing a synthesis gas containing carbon monoxide and hydrogen by using carbon dioxide and hydrogen;

a hydrocarbon production step of producing a hydrocarbon (C5+) by using the synthesis gas; and a first separation step of separating a recycle gas containing a light hydrocarbon (C4−) having 4 or less carbon atoms from an effluent from the hydrocarbon production step, wherein in the synthesis gas production step, supply of the recycle gas is received and the recycle gas is also used for production of the synthesis gas.

The invention claimed is:

1. A hydrocarbon production apparatus comprising:

a synthesis gas production unit structured to produce a synthesis gas containing carbon monoxide and hydrogen by using carbon dioxide and hydrogen, wherein the synthesis gas also contains carbon dioxide;

a hydrocarbon production unit structured to produce a hydrocarbon by using the synthesis gas; and a first separator structured to separate a recycle gas containing a light hydrocarbon having 4 or less carbon atoms from an effluent from the hydrocarbon production unit;

a second separator structured to separate carbon dioxide from the synthesis gas, wherein the carbon dioxide separated by the second separator is directly supplied to the synthesis gas production unit;

a reformer structured to reform the light hydrocarbon into methane; and a product production unit structured to receive supply of the hydrocarbon from the hydrocarbon production unit and produce a hydrocarbon product, wherein the synthesis gas production unit is structured to receive supply of the recycle gas and also use the recycle gas for production of the synthesis gas;

the synthesis gas production unit is structured to receive supply of the carbon dioxide separated by the second separator and use the carbon dioxide for production of the synthesis gas;

the synthesis gas production unit is structured to receive supply of the methane generated by the reformer and also use the methane for production of the synthesis gas;

the product production unit is structured to by-produce the light hydrocarbon together with the hydrocarbon product; and the reformer is structured to receive supply of the light hydrocarbon from the product production unit and also reform the light hydrocarbon into methane.

2. The hydrocarbon production apparatus according to claim 1, wherein the hydrocarbon production unit is structured to receive supply of a part of the recycle gas from the first separator and also use the recycle gas for production of the hydrocarbon.

3. The hydrocarbon production apparatus according to claim 1, wherein the recycle gas also contains carbon monoxide, the hydrocarbon production apparatus comprises a fifth separator structured to separate carbon monoxide from the recycle gas, and the hydrocarbon production unit is structured to receive supply of the carbon monoxide separated by the fifth separator and also use the carbon monoxide for production of the hydrocarbon.

4. The hydrocarbon production apparatus according to claim 1, wherein the recycle gas also contains hydrogen, carbon monoxide, and carbon dioxide, the hydrocarbon production apparatus comprises a third separator structured to separate hydrogen, carbon monoxide, and carbon dioxide from the recycle gas, the second separator is structured to receive supply of hydrogen, carbon monoxide, and carbon dioxide from the third separator and separate the hydrogen, the carbon monoxide, and the carbon dioxide into hydrogen and carbon monoxide, and carbon dioxide, and the hydrocarbon production unit is structured to receive supply of the hydrogen and carbon monoxide separated by the second separator and also use the hydrogen and the carbon monoxide for production of the hydrocarbon.

5. The hydrocarbon production apparatus according to claim 1, wherein the recycle gas also contains hydrogen, carbon monoxide, and carbon dioxide, the hydrocarbon production apparatus comprises a third separator structured to separate hydrogen, carbon monoxide, and carbon dioxide from the recycle gas, and a fourth separator structured to receive supply of hydrogen, carbon monoxide, and carbon dioxide from the third separator and separate the hydrogen, the carbon monoxide, and the carbon dioxide into hydrogen and carbon monoxide, and carbon dioxide, and the hydrocarbon production unit is structured to receive supply of the hydrogen and carbon monoxide separated by the fourth separator and also use the hydrogen and the carbon monoxide for production of the hydrocarbon.

6. The hydrocarbon production apparatus according to claim 1, wherein the recycle gas also contains hydrogen, the hydrocarbon production apparatus comprises a sixth separator structured to separate hydrogen from the recycle gas, and the hydrocarbon production unit is structured to receive supply of the hydrogen separated by the sixth separator and also use the hydrogen for production of the hydrocarbon.

7. The hydrocarbon production apparatus according to claim 1, wherein the recycle gas also contains hydrogen, carbon monoxide, and carbon dioxide, the hydrocarbon production apparatus comprises a fifth separator structured to separate carbon monoxide from the recycle gas, and a seventh separator structured to receive supply of the recycle gas from which carbon monoxide is separated by the fifth separator and separate hydrogen and carbon dioxide from the recycle gas, the second separator is structured to receive supply of the hydrogen and carbon dioxide separated by the seventh separator and separate the hydrogen and the carbon dioxide into hydrogen and carbon dioxide, and the hydrocarbon production unit is structured to receive supply of the carbon monoxide separated by the fifth separator and the hydrogen separated by the second separator and also use the carbon monoxide and the hydrogen for production of the hydrocarbon.

8. The hydrocarbon production apparatus according to claim 1, wherein the recycle gas also contains hydrogen and carbon monoxide, the hydrocarbon production apparatus comprises a fifth separator structured to separate carbon monoxide from the recycle gas, and a sixth separator structured to receive supply of the recycle gas from which carbon monoxide is separated by the fifth separator and separate hydrogen from the recycle gas, and the hydrocarbon production unit is structured to receive supply of the carbon monoxide separated by the fifth separator and the hydrogen separated by the sixth separator and also use the carbon monoxide and the hydrogen for production of the hydrocarbon.

9. The hydrocarbon production apparatus according to claim 1, wherein the recycle gas also contains hydrogen, carbon monoxide, and carbon dioxide, the hydrocarbon production apparatus comprises a seventh separator structured to separate hydrogen and carbon dioxide from the recycle gas, and a fifth separator structured to receive supply of the recycle gas from which hydrogen and carbon dioxide are separated by the seventh separator and separate carbon monoxide from the recycle gas, the second separator is structured to receive supply of the hydrogen and carbon dioxide separated by the seventh separator and separate the hydrogen and the carbon dioxide into hydrogen and carbon dioxide, and the hydrocarbon production unit is structured to receive supply of the carbon monoxide separated by the fifth separator and the hydrogen separated by the second separator and also use the carbon monoxide and the hydrogen for production of the hydrocarbon.

10. The hydrocarbon production apparatus according to claim 1, wherein the recycle gas also contains hydrogen and carbon monoxide, the hydrocarbon production apparatus comprises a sixth separator structured to separate hydrogen from the recycle gas, and a fifth separator structured to receive supply of the recycle gas from which hydrogen is separated by the sixth separator and separate carbon monoxide from the recycle gas, and the hydrocarbon production unit is structured to receive supply of the hydrogen separated by the sixth separator and the carbon monoxide separated by the fifth separator and also use the hydrogen and the carbon monoxide for production of the hydrocarbon.

11. A hydrocarbon production method comprising:

a synthesis gas production step of producing a synthesis gas containing carbon monoxide and hydrogen by using carbon dioxide and hydrogen, wherein the synthesis gas also contains carbon dioxide;

a hydrocarbon production step of producing a hydrocarbon by using the synthesis gas; and a first separation step of separating a recycle gas containing a light hydrocarbon having 4 or less carbon atoms from an effluent from the hydrocarbon production step;

a second separation step of separating carbon dioxide from the synthesis gas, wherein the carbon dioxide separated by the second separation step is directly supplied to the synthesis gas production step;

a reforming step of reforming the light hydrocarbon into methane; and a product production step of receiving supply of the hydrocarbon from the hydrocarbon production step and producing a hydrocarbon product, wherein in the synthesis gas production step, supply of the recycle gas is received, and the recycle gas is also used for production of the synthesis gas;

in the synthesis gas production step, supply of the carbon dioxide separated by the second separation step is received, and the carbon dioxide is also used for production of the synthesis gas;

in the synthesis gas production step, supply of the methane generated by the reforming step is received, and the methane is also used for production of the synthesis gas;

in the product production step, the light hydrocarbon is by-produced together with the hydrocarbon product; and in the reforming step, supply of the light hydrocarbon is received from the product production step, and the light hydrocarbon is also reformed into methane.

12. The hydrocarbon production apparatus according to claim 1, wherein the synthesis gas production unit receives supply of hydrogen from a water electrolysis module.

13. The hydrocarbon production method according to claim 11, wherein the synthesis gas production step receives supply of hydrogen from a water electrolysis module.

14. The hydrocarbon production apparatus according to claim 12, wherein at least one of the synthesis gas production unit and the hydrocarbon production unit produces water, and wherein the water electrolysis module receives a supply of the water and produces hydrogen and oxygen by electrolysis of the water.

15. The hydrocarbon production method according to claim 13, wherein at least one of the synthesis gas production step and the hydrocarbon production step produces water, and wherein the water electrolysis module receives a supply of the water and produces hydrogen and oxygen by electrolysis of the water.

16. The hydrocarbon production apparatus according to claim 1, wherein at least one of the synthesis gas production unit and the hydrocarbon production unit produces water, and wherein the reformer receives a supply of the water and uses the water to reform the light hydrocarbon into methane.

17. The hydrocarbon production method according to claim 11, wherein at least one of the synthesis gas production step and the hydrocarbon production step produces water, and wherein the reforming step receives a supply of the water and uses the water to reform the light hydrocarbon into methane.

* * * * *